United States Patent
Maloisel et al.

(10) Patent No.: US 11,285,460 B2
(45) Date of Patent: Mar. 29, 2022

(54) SEPARATION MATRICES FOR PURIFICATION OF BIOLOGICAL PARTICLES

(71) Applicant: Cytiva BioProcess R&D AB, Uppsala (SE)

(72) Inventors: Jean-Luc Maloisel, Uppsala (SE); Karolina Busson, Uppsala (SE); Karol Lacki, Uppsala (SE); Bjorn Noren, Uppsala (SE); Helena Skoglar, Uppsala (SE)

(73) Assignee: CYTIVA BIOPROCESS R&D AB, Uppsala (SE)

( * ) Notice: Subject to any disclaimer, the term of this patent is extended or adjusted under 35 U.S.C. 154(b) by 170 days.

(21) Appl. No.: 15/120,845

(22) PCT Filed: Feb. 18, 2015

(86) PCT No.: PCT/SE2015/050186
§ 371 (c)(1),
(2) Date: Aug. 23, 2016

(87) PCT Pub. No.: WO2015/137860
PCT Pub. Date: Sep. 17, 2015

(65) Prior Publication Data
US 2016/0367966 A1   Dec. 22, 2016

(30) Foreign Application Priority Data

Mar. 14, 2014   (SE) .................................. 1450290-0

(51) Int. Cl.
*B01D 15/12*   (2006.01)
*B01D 15/20*   (2006.01)
(Continued)

(52) U.S. Cl.
CPC ........ *B01J 20/3293* (2013.01); *B01D 15/125* (2013.01); *B01D 15/203* (2013.01);
(Continued)

(58) Field of Classification Search
CPC ... B01J 20/24; B01J 20/26; B01J 20/22; B01J 20/282; B01J 20/285; B01J 20/3206;
(Continued)

(56) References Cited

U.S. PATENT DOCUMENTS 6,090,288 A     7/2000  Berglund
6,159,591 A *   12/2000 Beihoffer .......... A61F 13/15203
                                                428/327
(Continued)

FOREIGN PATENT DOCUMENTS

CN     1678903 A     10/2005
CN     102958602 A    3/2013
(Continued)

OTHER PUBLICATIONS

Hayes et al. Core-shell particles: Preparation, fundamentals and applications in high performance liquid chromatography. J. Chroma. A. vol. 1357, (Aug. 2014) p. 36-52. (Year: 2014).*
(Continued)

*Primary Examiner* — Benjamin L Lebron
(74) *Attorney, Agent, or Firm* — Eversheds Sutherland (US) LLP (57) ABSTRACT

The invention discloses a separation matrix for purification of biological particles, comprising a plurality of particles having a porous core entity and a porous shell entity covering the core entity, wherein the core entity comprises at least 50 micromole/ml primary amines present on covalently attached ligands displaying at least two primary amines per ligand and the shell entity comprises less than 20 micromole/ml primary amines The invention further dis-
(Continued)

closes a method of purifying biological particles and a method of manufacturing a separation matrix.

11 Claims, 6 Drawing Sheets

(51) Int. Cl.
| | |
|---|---|
| *B01D 15/30* | (2006.01) |
| *B01D 15/36* | (2006.01) |
| *B01J 20/28* | (2006.01) |
| *B01J 20/286* | (2006.01) |
| *B01J 20/32* | (2006.01) |
| *C07K 1/22* | (2006.01) |
| *C07K 14/765* | (2006.01) |
| *C07K 14/77* | (2006.01) |
| *C12N 1/20* | (2006.01) |

(52) U.S. Cl.
CPC ......... *B01D 15/305* (2013.01); *B01D 15/363* (2013.01); *B01J 20/286* (2013.01); *B01J 20/28019* (2013.01); *B01J 20/327* (2013.01); *B01J 20/3212* (2013.01); *B01J 20/3219* (2013.01); *B01J 20/3248* (2013.01); *B01J 20/3278* (2013.01); *C07K 1/22* (2013.01); *C07K 14/765* (2013.01); *C07K 14/77* (2013.01); *C12N 1/20* (2013.01)

(58) Field of Classification Search
CPC .. B01J 20/3208; B01J 20/321; B01J 20/3217; B01J 20/3219; B01J 20/3285; B01J 20/3242; B01J 20/3289; B01J 20/3248; B01J 20/3251; B01J 20/3293; B01J 20/3295; B01J 20/28019; B01J 20/286; B01J 20/3212; B01J 20/327; B01J 20/3278; B01D 15/125; B01D 15/203; B01D 15/305; B01D 15/363; C07K 1/22; C07K 14/765; C07K 14/77; C12N 1/20
See application file for complete search history.

(56) References Cited

U.S. PATENT DOCUMENTS

| | | | |
|---|---|---|---|
| 7,208,093 B2 | 4/2007 | Berg et al. | |
| 8,070,958 B2 | 12/2011 | Bergstrom et al. | |
| 8,685,248 B2 | 4/2014 | Glad | |
| 2005/0031850 A1* | 2/2005 | Mitchell | A61F 13/53 |
| | | | 428/327 |
| 2005/0285073 A1* | 12/2005 | Singh | A61K 9/5094 |
| | | | 252/62.54 |
| 2007/0125711 A1* | 6/2007 | Bergstrom | B01J 20/286 |
| | | | 210/656 |
| 2007/0151928 A1 | 7/2007 | Glad | |
| 2009/0277839 A1* | 11/2009 | Linford | B01J 13/02 |
| | | | 210/656 |
| 2011/0065900 A1* | 3/2011 | Johansson | B01D 15/363 |
| | | | 530/387.3 |
| 2012/0077249 A1 | 3/2012 | Ramaswamy et al. | |
| 2012/0193278 A1 | 8/2012 | Kozlov et al. | |
| 2012/0252091 A1* | 10/2012 | Rasmussen | C07K 1/22 |
| | | | 435/183 |
| 2012/0292244 A1* | 11/2012 | Harrold | B01J 20/3293 |
| | | | 210/263 |
| 2012/0309618 A1 | 12/2012 | Bergstrom et al. | |

FOREIGN PATENT DOCUMENTS

| | | |
|---|---|---|
| EP | 1235749 A1 | 9/2002 |
| GB | 2445579 A | 7/2008 |
| WO | 2005/082483 A1 | 9/2005 |
| WO | 2008/028218 A | 3/2008 |
| WO | 2009131526 A1 | 10/2009 |
| WO | 2009/145722 A1 | 12/2009 |
| WO | 2011/140406 A1 | 11/2011 |
| WO | 2012/005664 A1 | 1/2012 |
| WO | 2013/028330 A2 | 2/2013 |
| WO | 2015/137860 A1 | 9/2015 |

OTHER PUBLICATIONS

International Search Report and Written Opinion regarding International Application No. PCT/SE2015/050186, dated Jun. 23, 2015, 12 pages.

Extended European Search Report received for European Patent Application No. 15761376.1, dated Mar. 7, 2017, 10 pages.

International Preliminary Report on Patentability received for PCT Patent Application No. PCT/SE2015/050186, dated Sep. 14, 2016, 6 pages.

First Office Action for Chinese Patent Appl. No. 201580013843.8, filed Feb. 18, 2015, 21 pages, dated Apr. 28, 2018.

Office Action for Japanese Patent Appl. No. 2016-555958, 21 pages, dated Jan. 8, 2019.

Second Office Action for Chinese Patent Appl. No. 201580013843. 8, filed Feb. 18, 2015, 7 pages, dated Feb. 28, 2019.

First Examination Report (FER) for India Patent Application No. 201617023650, dated Oct. 7, 2019, 7 pages.

* cited by examiner

SEPARATION MATRICES FOR PURIFICATION OF BIOLOGICAL PARTICLES

CROSS-REFERENCE TO RELATED APPLICATIONS

This application is a filing under 35 U.S.C. 371 of international application number PCT/SE2015/050186, filed Feb. 18, 2015, which claims priority to SE application number 1450290-0, filed Mar. 14, 2014, the entire disclosures of each of which are hereby incorporated by reference.

TECHNICAL FIELD OF THE INVENTION

The present invention relates to separation matrices for purification of biological particles, and more particularly to separation matrices for purification of vaccine antigens, e.g. virus particles. The invention also relates to use of separation matrices for purification of biological particles, to methods for purification of biological particles and to methods of manufacturing separation matrices.

BACKGROUND OF THE INVENTION

In many vaccines the antigen is composed of particles having a size considerably larger than protein molecules. This is the case for e.g. viruses, virus-like particles, bacteria and plasmid antigens. In the manufacturing process of these antigens they are produced together with proteins and other contaminating species of considerably smaller size than the antigens. These species can be e.g. egg proteins for egg-derived antigens and host cell proteins as well as culture media components for antigens produced in cell cultures. These proteins are present in high amounts and have to be removed during processing of the antigen, as they can e.g. give rise to allergic reactions.

Size exclusion chromatography has traditionally been used for size-based separation of antigens and contaminating proteins, but increasing demands on throughput and process economics have prompted the search for alternative methods. Recently, a class of chromatography media has been made available where an inner core of chromatography beads is functionalized with ligands having both a positive charge and a hydrophobic moiety, while an outer shell is inert and has a pore size smaller than a virus antigen. The contaminating proteins can penetrate through the shell into the core where they are strongly bound by the ligands and the virus particles will pass through the column without binding and can be collected in the flowthrough. Such media are commercially available from GE Healthcare Bio-Sciences AB under the name of Capto™ Core 700. Similar media have also been described in WO9839364, WO2009131526 and U.S. Pat. No. 7,208,093, which are hereby incorporated by reference in their entireties.

Most antigens are produced under conditions where the ionic strength is close to what is normal under physiological conditions, i.e. about 0.1-0.2 mol/l corresponding to conductivities of about 10-20 mS/cm. Under these conditions the binding capacity of existing products, particularly those relying on charge interaction mechanisms, is limited and it would be desirable to increase the binding capacity at high salt conditions in order to avoid dilutions or buffer exchanges before application of the feed to the chromatography media.

Further, it is desirable to re-use the chromatography media for a large number of separation cycles. This necessitates a cleaning (also called regeneration) of the media between the cycles to remove the adsorbed proteins. With hydrophobic moieties present, this can be challenging and may require addition of solvents such as alcohols, which causes a fire and explosion hazard during operation. This problem becomes further accentuated in cases where the hydrophobicity of the ligands is increased in order to increase the binding capacity at high ionic strengths.

Accordingly there is a need for new matrices allowing the purification of vaccine antigens and other biological particles from contaminating proteins at high ionic strengths and at the same time allowing a safe and convenient cleaning of the matrices before re-use.

SUMMARY OF THE INVENTION

One aspect of the invention is to provide a regeneratable separation matrix capable of binding high amounts of proteins at high ionic strengths and allowing biological particles to be retrieved in a flowthrough fraction. This is achieved with a separation matrix as defined in claim 1.

One advantage is that the matrix still has a high binding capacity for common contaminating proteins at ionic strengths of 100-200 mM and higher. Further advantages are that the matrix does not bind virus particles or virus-like particles and that a wide range of tenaciously adsorbed contaminating proteins can be easily removed by the application of solvent-free regenerating solutions, allowing convenient reuse of the matrix.

A second aspect of the invention is to provide a method for separation of biological particles. This is achieved with a method as defined in the claims. Advantages of this method include the possibility to bind high amounts of contaminating proteins at high ionic strengths and the ease of regeneration of the matrix. A third aspect of the invention is to provide a use of a separation matrix for purification of biological particles. This is achieved with a method as defined in the claims.

A fourth aspect of the invention is to provide a method of manufacturing a separation matrix suitable for purification of biological particles. This is achieved with a method as defined in the claims.

Further suitable embodiments of the invention are described in the dependent claims.

FIGURES

FIG. 4 shows chip electrophoresis data for extracts of E Coli-fouled Capto™ Core 700 after regeneration with different regeneration solutions. Lanes: 1—Mw markers; 2—M NaOH; 3—2 M NaOH; 4—2 M NaOH+30% 2-propanol; 5—30% 2-propanol; 6—1 M NaOH+20% 1-propanol; 7—1 M NaOH+10% 1-propanol; 8—1 M NaOH+5% 1-propanol; 9—20% 1-propanol; 10—0.5 M NaOH/10 mM HCl/0.5M NaOH; 11—1M NaOH/10 mM HCl/1M NaOH; 12—20% propylene glycol; 13—40% propylene glycol; 14—1 M NaOH+20% propylene glycol; 15—1M NaOH+

40% propylene glycol; 16—8 M urea/1MNaOH;17—1 Murea/1 M NaOH; 18—8 M urea; 19—8 M urea+0 M citric acid; 20—8 M urea+1 M NaCl+0.1M citric acid.

DETAILED DESCRIPTION OF EMBODIMENTS

Figure 1:
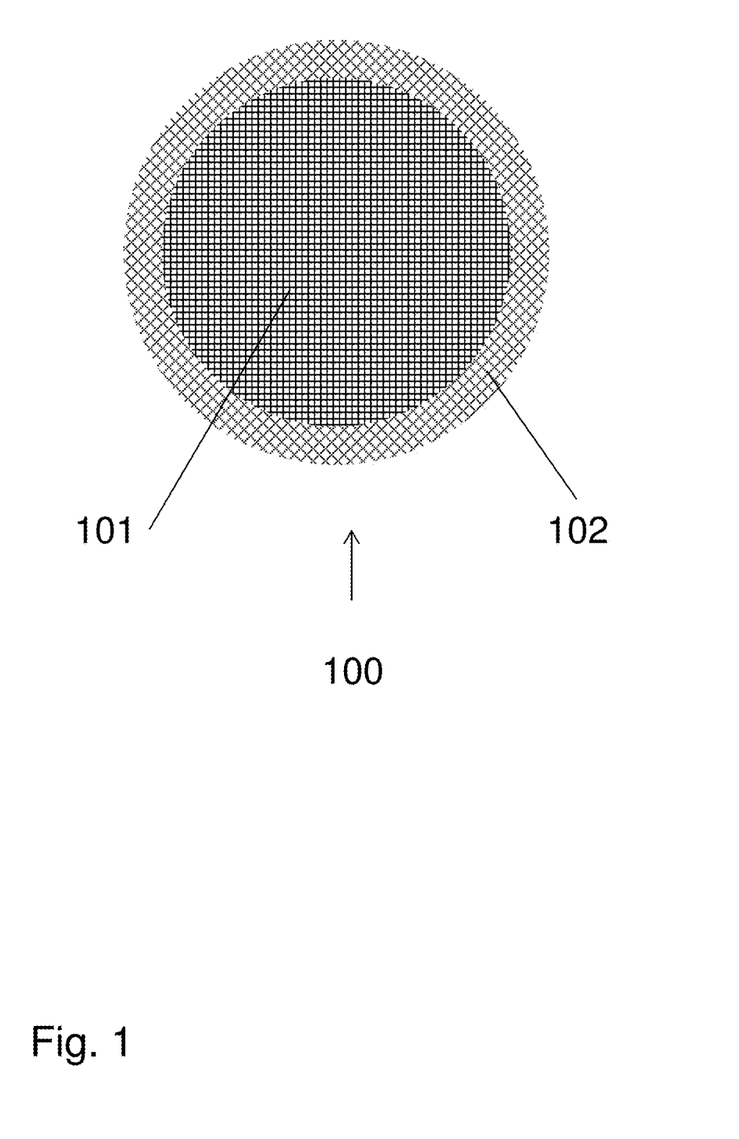
FIG. 1 shows a schematic structure of the matrix of the invention.
Figure 2:
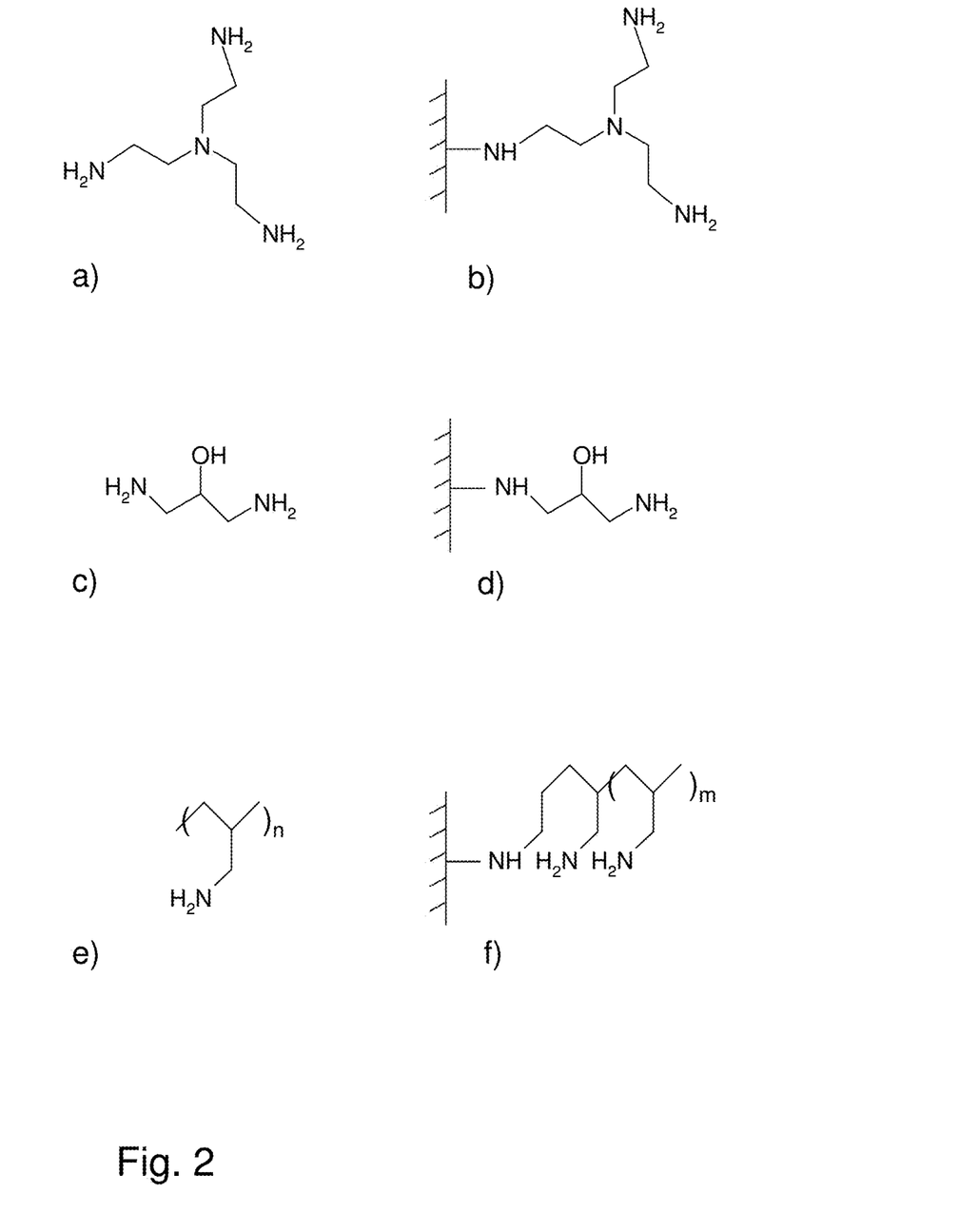
FIG. 2 shows examples of ligands: a) tris(2-aminoethyl) amine ligand precursor, b) tris(2-aminoethyl)amine coupled ligand, c) 1,3-diamino-2-propanol ligand precursor, d) 1,3-diamino-2-propanol coupled ligand, e) polyallylamine ligand precursor and f) polyallylamine coupled ligand.
Figure 3:
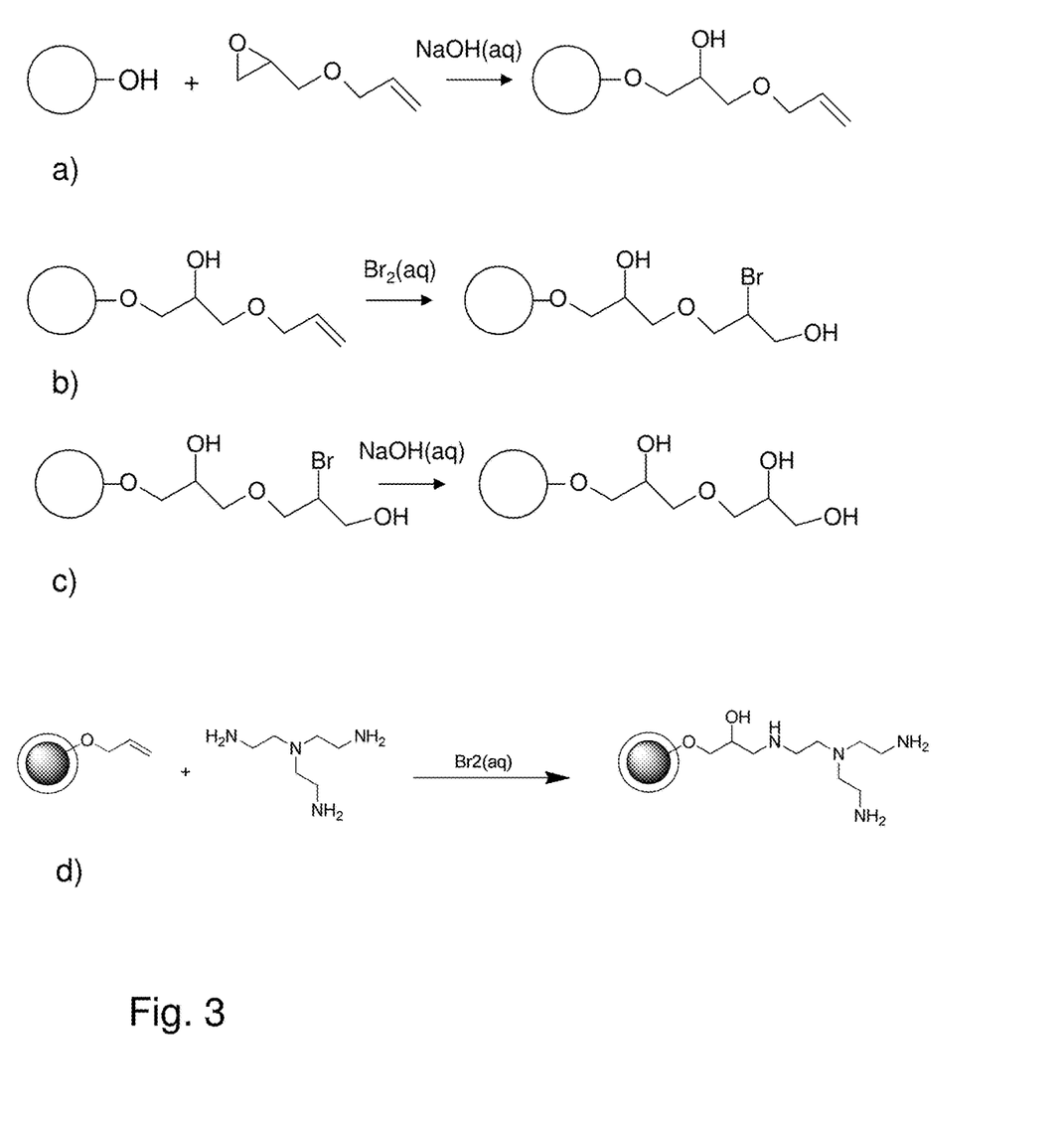
FIG. 3 shows examples of synthesis routes of the invention, a) allylation, b) bromination, c) inactivation and d) coupling.

In one aspect the present invention, as illustrated by FIGS. 1 and 2, discloses a separation matrix for purification of biological particles, which comprises a plurality of particles 100 having a porous core entity 101 and a porous shell entity 102 covering the core entity. Suitably, each particle 100 within the plurality can have a porous core entity 101 covered by a porous shell entity 102. The core entity comprises at least 50 micromole/ml primary amines present on covalently attached ligands displaying at least two primary amines per ligand and the shell entity comprises less than 20 micromole/ml primary amines, such as less than 10 or less than 1 micromole/ml. The term displaying means that the ligands have at least two primary amines per ligand when the ligand is in the attached state. The presence of a shell entity with a lower ligand content than the core entity can e.g. be detected by microscopy. The particles can be contacted with an acidic fluorescent dye (e.g. fluorescein), or a fluorescent dye reactive towards primary amines (e.g. 5-carboxyfluorescein succinimidyl ester), and the spatial distribution of the fluorescence can be measured in a confocal microscope. Alternatively the particles can be dyed, embedded in a resin, sectioned with a microtome and observed in a conventional microscope. With both methods, the relative ligand concentrations in the two regions can be assessed by densitometry and absolute concentrations calculated by multiplication with the total ligand content for the matrix as determined e.g. by titration methods or spectroscopic methods well known in the art.

In certain embodiments, the matrix is capable of binding at least 20 mg ovalbumin per ml matrix, such as at least 30 or at least 40 mg ovalbumin, in an aqueous buffer having a conductivity of at least 10 mS/cm, such as at least 20 mS/cm. 10 mS/cm corresponds to about 0.1 M NaCl and 20 mS/cm to about 0.2 M NaCl. As most physiological systems such as cell cultures, egg fluids, blood plasma, milk etc have conductivities in these ranges, it is advantageous to have a high capacity for protein binding, as exemplified by ovalbumin, under these conditions. The matrix can also be capable of binding at even higher conductivities such as e.g. 20-30 or 30-40 mS/cm, which is of interest e.g. when the liquid is an eluate from an ion exchange or a HIC matrix. The test for binding capacity can suitably be carried out in a Tris buffer at pH 7.5, using a static capacity test with 60 min contact time as described in the Examples.

In some embodiments, said ligands display at least two, such as at least three or at least four primary amines per ligand. It appears that the number of available primary amines per ligand is advantageous for the binding capacity at high ionic strengths and that it should be at least two. It can further be advantageous if the primary amines are bound to primary carbon atoms with only one bond to another carbon, such as in aminomethyl- or aminoethyl groups, $H_2N—CH_2—$ and $H_2N—CH_2—CH_2—$ respectively. This provides better accessibility to proteins compared to primary amines bound to secondary or tertiary carbons. The ligands can be of different molecular weight, monomeric or polymeric and may form part of larger structures.

In certain embodiments, the ligands are attached to the core entity via secondary or tertiary amine links Amine links are chemically stable and easy to achieve by coupling between an amine on a ligand precursor and an electrophilic group on a support material, such as e.g. an epoxide or a halohydrin. The ligand precursor can suitably be a species with at least three primary amines, such that one primary amine is consumed to make the attachment link and at least two remaining primary amines per ligand are displayed in the coupled matrix.

In some embodiments, the combined content of nitrogen and oxygen atoms in said ligands is at least 20 wt %. The content of primary amine nitrogen in the attached ligands can advantageously be at least 18 wt %. The ratio of displayed primary amines to the total amount of nitrogen atoms can be at least 0.5, such as at least 0.7 or at least 0.9. With these ratios the ligands are hydrophilic, i.e. they do not bind proteins irreversibly, and the primary amine content is high enough to give high binding at high ionic strengths.

In certain embodiments, the ligands are selected from the group consisting of tris(2-aminoethyl)amine and polyallylamine. These ligands are hydrophilic and display a plurality of primary amines even when attached via an amine The ligands can e.g. comprise polyallylamine of molecular weight at least 1 kDa, such as at least 5 kDa or at least 10 kDa. The polyallylamine can suitably be non-crosslinked to provide mobility and access to proteins. The attachment can be in a single point or by multipoint attachment. Single point attachment can e.g. be achieved by graft polymerization or by coupling via a reactive end-group on the polyallylamine Multipoint attachment can be achieved by coupling the polyallylamine via the amines to electrophilic groups or aldehydes on the core entities according to methods known in the art.

In some embodiments, the shell entity has an average thickness of 1 to 10 micrometers, such as 1 to 6 micrometers. A minimum shell thickness ensures that ligands are not available for binding to the biological particles on the outside of the separation matrix particles, while the shell thickness should suitably not be too high, in order to maximize the binding capacity for proteins in the core entity. The particles can be substantially spherical, e.g. with a volume-weighted average diameter of 15-400 micrometers, and in this case the shell entity can have an average thickness of 0.5 to 6% of the volume-weighted average diameter of the particles. If the particles are non-spherical, the shell entity can have an average thickness of 0.5 to 6% of the sphere-equivalent diameter of the particles. The average sphericity of the particles, defined as the ratio of the surface area of a sphere (having the same volume as a given particle) to the surface area of the particle, can be at least 0.9, such as at least 0.97. The shell thickness can be determined microscopically on dyed particles, as discussed above. The separation matrix particles can e.g. be manufactured according to the method disclosed below, in which case the thickness of the shell can be controlled by a partial deactivation process.

In certain embodiments, the shell entity has a molecular weight cutoff for globular proteins of 60 to 1000 kDa, such as 100-1000 or 400-800 kDa. This is advantageous to allow rapid mass transport of contaminating proteins into and out of the particles, while preventing the biological particles from reaching the core entity. The cutoff can e.g. be measured by comparing binding capacities for proteins of different molecular weight under conditions where they bind to the ligands.

In a second aspect the present invention discloses a method for purification of biological particles, comprising the steps of a) providing a separation matrix according to any embodiment disclosed above;
b) contacting said matrix with a liquid comprising biological particles and at least one contaminant protein, such that said contaminant protein binds to said matrix;
c) separating said liquid from said matrix and recovering said liquid with purified biological particles.

The liquid can be e.g. an allantoic fluid from eggs, a cell culture supernatant, a cell lysate etc and it can e.g. have a conductivity of at least 10 mS/cm or even at least 15 mS/cm, which means that the liquid does not have to be extensively diluted. In addition to contaminant protein(s), also other contaminants such as e.g. DNA and/or endotoxins may be bound to the matrix and thus removed. The method may be a chromatographic method, where the matrix is packed into a column, but it may also be a batch adsorption method (e.g. using a magnetic matrix) or e.g. an expanded bed adsorption method (e.g. using matrix particles comprising high density filler particles). When the matrix is used as a packed bed in a column, the column may have a bed height of 1 mm-1 m, such as 1 cm to 30 cm or 1 cm to 10 cm. The packed bed may comprise only the matrix of the invention but mixed beds with other matrices are also contemplated.

In certain embodiments the method further comprises the steps of d) regenerating said matrix by contacting it with a regeneration solution, and;
e) repeating steps a)-c) at least once, such as at least five, at least 10 or at least 50 times. The regeneration solution can suitably be free from organic solvents or contain less than 15 wt %, such as less than 5 wt % or less than 1 wt %, flammable solvents, which is advantageous in that expensive explosion-proof equipment and localities does not have to be used in the process. In addition, it also provides a more environmentally friendly process.

In some embodiments the regeneration solution comprises alkali, such as NaOH, of e.g. 0.1-2 M concentration, such as 0.5-2 M. Alkali, and in particular NaOH, is a useful cleaning agent in that it hydrolyses proteins and in that after washing and neutralization it does not leave any potentially toxic residuals.

In certain embodiments the residual protein content in the matrix after step d) is less than 100 micrograms/ml matrix. The residual protein amount can be determined by a total extraction by boiling in a 0.5% SDS+28 mM DTT extraction solution and detection of the extracted proteins by chip electrophoresis, as described in the Examples.

In some embodiments the biological particles are selected from the group consisting of viruses, virus-like particles, cells, organelles and plasmids. In certain embodiments at least 40 mg/ml, such as at least 60 mg/ml, of said contaminant protein binds to the matrix. It is advantageous if the matrix can be loaded with a large amount of liquid, which is possible with the new matrix. As is well known, the loading should not exceed the binding capacity of the matrix as this would lead to breakthrough and consequently poor removal.

In some embodiments the liquid comprises a buffering substance. This buffering substance may e.g. comprise buffering cations, such as Tris, Bis-Tris, Tricine or piperazine, and/or monovalent buffering anions, such as acetate, lactate etc. It can be advantageous if the liquid does not comprise polyvalent anions, e.g. phosphate, as they may interact too strongly with the ligands under some conditions.

In certain embodiments the pH of the liquid is 6.0-8.5, such as 6.5-8.5 or 6.5-8.0. When live/viable biological particles are to be purified, they are highly sensitive to pH, which in these cases limits the usable range.

In some embodiments the contaminant protein is an albumin, such as ovalbumin or serum albumin. Albumins are common contaminant proteins both in egg-derived feeds and in cell cultures.

In certain embodiments the biological particles comprise an influenza virus. The liquid can e.g. comprise allantoic fluid derived from fertilized eggs or alternatively it can comprise a cell culture supernatant or a cell lysate.

In some embodiments the method can further comprise, before step b), a step a') of conditioning said liquid by crossflow filtration, such as ultrafiltration and/or microfiltration. Microfiltration, e.g. in hollow fibers, can be used to remove particulates which may otherwise clog the chromatography column. If desired, the liquid may also be subjected to ultrafiltration to increase the concentration of biological particles before applying the liquid to the matrix.

In certain embodiments the method can further comprise, after step c), a step c') of ion exchange chromatography, such as cation exchange chromatography. Any remaining positively charged contaminants can be removed with a subsequent cation exchange step. Subsequent steps may also comprise further flowthrough purification on matrices with functional core entitites and inert shell entitites.

In a third aspect the present invention discloses the use of a separation matrix as disclosed above for purification of biological particles. The biological particles can e.g. be selected from the group consisting of viruses, virus-like particles, cells, organelles and plasmids. The use can e.g. be in a method as disclosed above.

In a fourth aspect the invention discloses a method for manufacturing a separation matrix as disclosed above, comprising the steps of:

a) providing a plurality of porous polysaccharide support particles, such as crosslinked agarose gel particles;
b) reacting said particles with an allylation reagent to obtain at least 50, at least 100 or at least 200 micromole/ml allyl groups covalently attached to the particles;
c) reacting said particles with a halogen for a period of up to 30 minutes and then with an alkaline aqueous solution;
d) coupling a ligand precursor comprising a plurality of primary amines to the remaining allyl groups.

The allylation reagent can be e.g. allyl glycidyl ether or an allyl halide, such as allyl bromide. The halogen is suitably bromine and can be applied in an aqueous solution. In step b), allyl groups are introduced uniformly throughout the particles, while in step b), the short contact time with the bromine only allows reaction between the allyl groups in the outermost part of each particle and the bromine The reaction with bromine causes the formation of bromohydrins, which in aqueous alkali are converted to hydrophilic, non-reactive diols, thus causing the formation of an inert shell entity. If the aqueous alkali solution comprises a polyol, the polyol may react with the bromohydrins and be immobilized as hydrophilic non-reactive moieties. Such methods can also be used to fine-tune the pore structure of the shell entity. The allyl groups in the interior are left unreacted and can then be used to couple ligands in what becomes the core entity. The thickness of the shell entity can be controlled primarily by the contact time with the halogen and by the amount of halogen used in step c).

In certain embodiments the support particles are substantially spherical, with a volume average diameter of 15-400 micrometers, such as 30-100 micrometers. The support particles can e.g. be made from dextran, agarose, agar, carrageenan, alginate, cellulose, konjac or other suitable polysaccharides. Agarose, agarose derivatives (e.g. hydroxyethyl agarose), agar and cellulose can be particularly suitable as they can conveniently be prepared with suitable porosity and rigidity. The support particles can also be crosslinked, either by straight forward crosslinking with a crosslinking agent such as epichlorohydrin or a diepoxide or by two-stage crosslinking such as described in U.S. Pat. No. 6,602,990. The latter method provides an improved rigidity.

In some embodiments the ligand precursor has at least three primary amines per molecule and is coupled to the allyl groups by first reacting the allyl groups with an aqueous halogen, e.g. bromine, and then under alkaline conditions with the ligand precursor.

In certain embodiments the ligand precursor is selected from the group consisting of tris(2-aminoethyl)amine and polyallylamine, e.g. polyallylamine of Mw at least 5 kDa, such as at least 10 kDa.

EXAMPLES

Example 1

Synthesis of Prototypes

Support Particles

The support particles used were highly crosslinked agarose beads, prepared according to the methods described in U.S. Pat. No. 6,602,990, which is hereby incorporated by reference in its entirety. The beads had a volume-weighted average diameter (D50,v) of 88 micrometers and a pore size distribution such that 69% of the pore volume was available to dextran molecules of Mw 110 kDa. This can also be expressed such that Kd for dextran 110 kDa on the beads was 0.69, when measured according to the methods described in "Handbook of Process Chromatography, A Guide to Optimization, Scale-Up and validation" (1997) Academic Press, San Diego. Gail Sofer & Lars Hagel eds.ISBN 0-12-654266-X, p. 368.

Allylations

Intermediate 5803

400 mL (g) of support particles were washed with six gel volumes distilled water and then three gel volumes with 50% NaOH. The gel was then sucked dry and transferred to a 2 L round bottom flask. 775 mL of 50% NaOH was added, mechanical propeller stirring was applied and the flask was immersed into a water bath at 50° C. After 30 minutes 128 mL of allyl glycidyl ether (AGE) was added. The reaction progressed for 17 h. The gel was washed with one gel volume distilled water, five gel volumes of ethanol and then eight gel volumes of distilled water.

Intermediate 5840

120 mL (g) of support particles were washed with six gel volumes distilled water, was dried by vaccum and transferred (90.7 g) to a 250 mL round bottom flask. 149.3 mL of 50% NaOH was added (11.8 M), mechanical propeller stirring was applied and the flask was immersed into a water bath at 50° C. After 30 minutes 36 mL of AGE was added. The reaction progressed for 17 h. The gel was washed with one gel volume distilled water, three gel volumes of ethanol and then eight gel volumes distilled water.

Intermediate 6383

200 mL (g) allylated support particles 5803, in distilled water, was washed on a glass filter with 3 gel volumes of 50% aqueous NaOH. The gel was then sucked dry and transferred to a 1 L round bottom flask. 388 mL of 50% aqueous NaOH was added, mechanical propeller stirring was applied and the flask was immersed into a water bath at 50° C. After 30 minutes 64 mL of allyl glycidyl ether was added and the reaction progressed for 16 h. The gel was washed with one gel volume of distilled water, 5 gel volumes of ethanol and then 8 gel volumes of distilled water.

Intermediate 3266A 256 mL(g) support particles were washed with distilled water and with 50% aqueous NaOH on a glass filter. The gel was then sucked dry and transferred to a 1 L round bottom flask. 200 mL of 50% aqueous NaOH was added, mechanical propeller stirring was applied and the flask was immersed into a water bath at 50° C. After 30 minutes 200 mL of AGE was added and the reaction progressed for 17 h. The gel was washed with distilled water, ethanol and distilled water.

Partial Bromination and Shell Inactivation

Intermediate 6478

192 g (mL) of allylated support particles, 6383, was transferred drained into a 3 L round bottomed flask together with 1728 mL of distilled water. Mechanical stirring was applied. A solution of 1000 μL bromine in 200 mL of water was prepared. The bromine solution (equivalent to the amount of allyl groups in a 5 μm shell of the 88 μm bead) was added slowly during approximately 2 minutes at a stirring speed of 300 rpm. After 20 minutes the gel was washed with 10 gel volumes of distilled water. 196 g (mL) of the partially activated gel was transferred drained into a 1 L round bottomed flask. 175.3 g of distilled water and 20.7 mL of 50% NaOH (1 M) were added and mechanical stirring was applied. The flask was immersed into a water bath at 50° C. and the reaction progressed for 18.5 h. The gel was then washed with 10 gel volumes of distilled water. 2×1 mL was titrated for remaining allyl content.

Intermediate 5860

115 g (mL) of allylated support particles, 5840, was transferred drained into a 2 L round bottomed flask together with 1035 mL of distilled water. Mechanical stirring was applied. A solution of 408 μL bromine in 100 mL of water was prepared. The bromine solution (equivalent to the allyls in a 5.5 μm shell of the 88 μm bead) was added slowly during approximately 2 minutes at a stirring speed of 250 rpm. Some of the bromine was lost during handling when pouring from the E-flask. Thereafter additions were made by using a plastic pipette. After 20 minutes the gel was washed with ten gel volumes distilled water.

116 g (mL) of the partially activated gel was transferred drained into a 500 mL round bottomed flask. 104 g of distilled water and 12.25 mL of 50% NaOH (1 M) were added and mechanical stirring was applied. The flask was immersed into a water bath at 50° C. and the reaction progressed for 16.5 h. The gel was then washed with ten gel volumes distilled water. 2×1 mL was titrated for remaining allyl content.

Intermediate 3266B 260 g (mL) of allylated support particles, 3266A, was transferred drained into a 3 L round bottomed flask together with 2300 mL of distilled water. Mechanical stirring was applied. A solution of 3.55 g bromine in 250 mL of water was prepared. The bromine solution was added slowly during stirring. After 5 minutes the gel was washed with distilled water.

The partially activated gel was transferred drained into a 1 L round bottomed flask. 250 mL 2 M aqueous NaOH were added and mechanical stirring was applied. The flask was immersed into a water bath at 50° C. and the reaction progressed for 17 h. The gel was then washed with distilled water. 2×1 mL was titrated for remaining allyl content.

Core Bromination 80 g (mL) of core allylated support particles, 6478, was transferred drained into a 500 mL E-flask with 80 mL of water and 3.2 g of sodium acetate. An aqueous solution of bromine was then added until a persistent yellow colour existed. Sodium formate (~2 g) was added to quench the excess of bromine The gel was washed with 10 gel volumes of distilled water.

Titration of allyl and remaining allyl (to determine inactivated shell thickness)

The gel is washed with water.

1.0 mL gel is measured with a cube and transferred to a suction flask with 9 mL of distilled water.

A saturated solution of bromine in water is added until a yellow color due to an excess of $Br_2$ is persisting.

The sample is left with magnetic stirring for 5 min

The sample is put under vacuum (water suction) with magnetic stirring to remove the excess of bromine The sample is then transferred to a titration beaker by rinsing the flask with 10 mL of distilled water.

2-3 drops of conc. HNO3 are added and the titration with 0.1 M AgNO3 for indirect measurement of allyl content is started.

The result is given as micromol/mL gel.

The theoretical shell thickness is calculated from a model where the residual allyl content after partial bromination and inactivation is assumed to be entirely in a core surrounded by a shell with no allyl groups. With a bead of 88 micrometer diameter and a shell thickness of x micrometers, the ratio of the allyl contents before and after bromination/inactivation will be $44^3/(44-x)^3$, from which x can be calculated.

TABLE 1

Allyl group content of allylated and of brominated/deactivated intermediates.

| Prototype | Allyl content μmol/mL | Theoretical shell thickness μm |
|---|---|---|
| 5840 | 210 | n/a |
| 5860 After partial bromination and inactivation | 164 | 3.5 |
| 6383 | 336 | n/a |
| 6478 After partial bromination and inactivation | 264 | 3.5 |
| 3266 A | 255 | n/a |
| 3266 B After partial bromination and inactivation | 190 | 4.0 |

Ligand Coupling 1,3-diamino-2-propanol coupling 24.8 g of 1,3-diamino-2-propanol (270 mmol, 34 eq) was transferred into a 100 mL round bottomed flask. The flask was immersed into a water bath at 60° C. to melt the ligand for 75 minutes.

30 mL (g) of core activated allylated support particles 6478 (7.92 mmol allyl, 1 eq) was transferred drained into the flask and mechanical propeller stirring (230 rpm) was applied. The reaction progressed for 17 h. After cooling down the flask, pH was measured to ~12. The gel was washed with 12 gel volumes of distilled water.

Tris(2-aminoethyl)amine coupling 40 mL (g) of core activated allylated base matrix 6478 (10.56 mmol allyl, 1 eq) was transferred drained into a 250 mL round bottomed flask. 39.6 mL of tris(2-aminoethyl)amine (264.3 mmol, 25 eq) was added and mechanical propeller stirring (200 rpm) was applied. The reaction progressed for 17 h. pH was measured to 8.8. The gel was washed with 10 gel volumes of distilled water.

Polyallylamine Coupling 37 mL (g) of core activated allylated base matrix, 3266B, was transferred drained into a 250 mL round bottomed flask. 11.3 g polyallylamine Mw 15 kDa (Aldrich, 283215) was dissolved in 20 ml distilled water+2 ml 50% aqueous NaOH and added to the flask. Mechanical propeller stirring (200 rpm) was applied and the reaction was allowed to proceed at 50 C for 17 h. The gel was first washed with 0.5 M HCl, then with 1 mM HCl and then with 10 gel volumes of distilled water.

Titration of Amine Content

The gel is washed with water.

The gel is washed with 3×0.5 M HCl and then with 3×1 mM HCl.

1.0 mL gel is measured with a cube and transferred to a titration cup with 19 mL of distilled water.

2-3 drops of conc. $HNO_3$ are added and titration with 0.1 M $AgNO_3$ for indirect measurement of amine content is started.

The result is given as micromol/mL gel.

TABLE 2

Amine content of core-shell prototypes.

| Prototype | Amine content μmol/mL | Ligand density μmol/mL |
|---|---|---|
| 1,3-diamino-2-propanol | 168 | 84 |
| Tris(2-aminoethyl)amine | 221 | 55 |
| Polyallylamine Mw 15 kDa | 210 | 0.8 |

Example 2

Binding Capacities for Proteins on Prototypes

Empty 96-well filter plates were filled with 6 μl gel per well. The method described in Table 3 was used during the plate experiments. The number of washes after incubation varied between two and three dependent of what was needed to wash out any unbound protein.

TABLE 3

Method for plate experiments

| Step | Volume (μl) | Buffer | Execution |
|---|---|---|---|
| Equilibration | 3x200 | Buffer | 1 min shake + vacuum |
| Protein addition | 100 + 100 | Protein solution + Buffer | 60 min shake + centrifugation |
| Wash | Xx200 | Buffer | 1 min shake + Centrifugation |

Analysis

Unbound protein is analyzed by absorbance at 280 nm and the concentration calculated from a calibration curve.

The amount of bound protein is calculated from the difference between the added protein and the amount of unbound protein.

From the concentration the capacity for each well is calculated.

The maximum capacity is expressed as g/L, this is based on calculations preparing the protein solution for each experiment not through UV-measurements in cuvette.

For each series a blank experiment was conducted with no protein added, to exclude any interference from other UV-absorbing materials.

Binding capacity results for BSA and Ovalbumin on PAA
Prototype: Polyallylamine
Ion capacity: 210 μmol/ml
Protein 1: BSA 2 g/l, IP~4.7
Protein 1: Ovalbumin 2 g/l, IP~4.7
Buffer system 1: 40 mM Tris pH 7.2-8.2
Buffer system 2: 20 mM Piperazine pH 6
Salt: NaCl

TABLE 4

Binding capacity (g/L) for BSA on Polyallylamine prototype.

| | NaCl (mM) | | | | | |
|---|---|---|---|---|---|---|
| | 0 | 250 | 500 | 750 | 1000 | 1250 |
| pH 7.2 40 mM Tris | 32 | 62 | 33 | 11 | 1 | 0 |
| pH 7.7 40 mM Tris | 32 | 62 | 44 | | 3 | 0 |
| pH 8.2 40 mM Tris | 44 | 61 | 40 | 14 | 3 | 0 |

As shown in Table 4 the polyallylamine prototype had the highest binding capacity for BSA at 250 mM NaCl. At 1250 mM NaCl the polyallylamine prototype has no capacity for BSA which indicates good possibilities for salt elution of BSA.

TABLE 5

Binding capacity (g/L) for BSA and Ovalbumin on Polyallylamine prototype.

| | | BSA |
|---|---|---|
| A | pH 6 20 mM Piperazine | 63 |
| B | pH 6 20 mM Piperazine 250 mM NaCl | 49 |
| C | pH 6 20 mM Piperazine 500 mM NaCl | 17 |
| | | Ovalbumin |
| E | pH 6 20 mM Piperazine | 65 |
| F | pH 6 20 mM Piperazine 250 mM NaCl | 41 |
| G | pH 6 20 mM Piperazine 500 mM NaCl | 18 |

When using Piperazine as a buffer system polyallylamine has the best binding capacity for both BSA and Ovalbumin at no salt, rows A and E in Table 5. However the capacity is still good with 250 mM NaCl.

Prototype: Polyallylamine
Ion capacity: 210 μmol/ml
Protein: Ovalbumin 2 g/l, IP~4.7
Buffer system: 20-40 mM Phosphate pH 7-7.5
Salt: NaCl

TABLE 6

Binding capacity (g/L) for Ovalbumin on the polyallylamine prototype.

| | Ovalbumin |
|---|---|
| 20 mM Phosphate + 0 mM NaCl, pH 7.0 | 20 |
| 20 mM Phosphate + 0 mM NaCl, pH 7.5 | 21 |
| 20 mM Phosphate + 150 mM NaCl, pH 7.0 | 13 |
| 20 mM Phosphate + 150 mM NaCl, pH 7.5 | 15 |
| 40 mM Phosphate + 300 mM NaCl, pH 7.0 | 5 |
| 40 mM Phosphate + 300 mM NaCl, pH 7.5 | 8 |
| 40 mM Phosphate + 500 mM NaCl, pH 7.0 | 7 |
| 40 mM Phosphate + 500 mM NaCl, pH 7.5 | 8 |

Prototype: Polyallylamine
Ion capacity: 210 μmol/ml
Protein 1: Ovalbumin 4 g/l, IP~4.7
Protein 2: BSA 4 g/L, IP~4.7
Buffer system: 40 mM Tris pH7.2-8.2
Salt: NaCl

TABLE 7

Binding capacity (g/L) for Ovalbumin and BSA on Polyallylamine prototype.

| | Ovalbumin | BSA |
|---|---|---|
| 40 mM Tris pH 7.2 + 250 mM NaCl | 73 | 73 |
| 40 mM Tris pH 7.7 + 250 mM NaCl | 65 | 70 |
| 40 mM Tris pH 8.2 + 250 mM NaCl | 52 | 63 |

In Table 6 polyallylamine shows the highest binding capacity for Ovalbumin when no salt is added, an influence by pH cannot be seen in the phosphate system.

Comparing Table 6 with Table 7 it is clear that polyallylamine favors capacity for Ovalbumin with a Tris buffer system more than a Phosphate buffer system. In the Tris system of Table 7 the capacity on polyallylamine increases with decreasing pH. The binding capacity for Ovalbumin is more affected by pH than it is for BSA.

Prototype: Polyallyl amine
Ion capacity: 210 μmol/ml
Protein: Ovalbumin 2 g/l, IP~4.7
Buffer system: 40 mM Tris pH7.2-7.5
Salt: NaCl

TABLE 8

Binding capacity (g/L) for Ovalbumin on the polyallylamine prototype

| | pH | 7.2 | 7.5 |
|---|---|---|---|
| A | 40 mM Tris + 0 mM NaCl | 66 | 66 |
| B | 40 mM Tris + 150 mM NaCl | 57 | 57 |
| C | 40 mM Tris + 300 mM NaCl | 45 | 44 |

Again it is shown that polyallylamine and Tris gives a high binding capacity for Ovalbumin, see Table. Even if the capacity decreases with salt addition it is still high.

Comparison of binding capacity for Ovalbumin on the polyallylamine prototype and Capto Core 700
Prototype: Polyallyl amine
Ion capacity: 210 μmol/ml
Buffer system 1: 50 mM Tris pH 7.4
Buffer system 2: 50 mM Phosphate pH 7.2
Salt: NaCl
Amount matrix/well: 6 μl

TABLE 10

Binding capacity (g/L) for Ovalbumin on the 1,3-diamino-2-propanol and Tris(2-aminoethyl)amine prototypes

| | | NaCl (mM) | | | | | | | | | | | |
|---|---|---|---|---|---|---|---|---|---|---|---|---|---|
| | | 1,3-diamino-2-propanol | | | | | | Tris(2-aminoethyl)amine | | | | | |
| | | 0 | 150 | 300 | 500 | 1000 | 1500 | 0 | 150 | 300 | 500 | 1000 | 1500 |
| A | 50 mM Tris pH 7.4 | 23 | 12 | 7 | 4 | 2 | | 32 | 20 | 12 | 6 | 2 | 1 |
| B | 50 mM Phosphate pH 7.2 | 1 | 1 | 1 | | | | 4 | 2 | | | | |

Reference media: Capto core 700
Ion capacity: 40-85 μmol/ml
Protein: Ovalbumin 3 g/l, IP~4.7
Buffer system: 40 mM Tris pH 7.2-7.5
Salt: NaCl

TABLE 9

Static binding capacity (g/L) for Ovalbumin on the polyallylamine prototype and Capto Core 700

| | | NaCl (mM) | | | | | |
|---|---|---|---|---|---|---|---|
| | | Polyallylamine | | | Capto ™ Core 700 | | |
| | | 0 | 150 | 250 | 0 | 150 | 250 |
| A | 40 mM Tris pH 7.2 | 101 | 83 | 69 | 29 | 22 | 22 |
| B | 40 mM Tris pH 7.5 | 101 | 82 | 70 | 27 | 23 | 22 |

Capto™ Core 700 (Ge Healthcare Bio-Sciences AB) is a commercially available product, based on highly crosslinked agarose beads of 85-90 micrometer volume-weighted average diameter, an inert shell with Mw cutoff 700 kDa and a core derivatised with octylamine ligands coupled via the amine nitrogen. The shell structure is very similar to the currently prepared prototypes and is known to give virtually zero interaction with e.g. virus particles.

In the Tris buffer systems the binding capacity for Ovalbumin is significantly better on polyallylamine.

Summary Polyallylamine

When running polyallylamine the isoelectric point (IP) for the ligand is suitably considered so the pH of the buffer is not close to the IP of the ligand, making it uncharged. The IP of polyallylamine is ~8.7.

Polyallylamine works very well for ovalbumin and BSA. Ovalbumin has been tested the most and it is clear that a Tris buffer system increases the capacity compared to a Phosphate buffer. The binding capacity of BSA is zero at 1.25 M NaCl, see Table 4, which indicates that it is possible to elute with salt. The characteristics of BSA and Ovalbumin are similar so it is likely that also Ovalbumin can be eluted from polyallylamine with salt.

Results 1.3-diamino-2-propanol and tris(2-aminoethyl) amine prototypes
Prototype: 1.3-diamino-2-propanol
Ligand density: 84 μmol/ml
Prototype: tris(2-aminoethyl)amine
Ligand density: 55 μmol/ml
Protein solution: Ovalbumin 2 g/L, IP~4.7

The 1,3-diamino-2-propanol and Tris(2-aminoethyl) amine prototypes bind at high salt concentrations, as can be seen in row A. Tris(2-aminoethyl)amine has a higher binding capacity for Ovalbumin and both prototypes favor Tris for binding of Ovalbumin.

Example 3

Cleaning of Fouled Prototypes

This study was performed in 96-well filter plates with 800 microliters well size. The plate wells were filled with 20 microliter matrix and fouled with an E. coli homogenate. Cleaning was performed with different regeneration liquids and the contaminants still left in the beads were forced into solution by boiling with 24 mM dithiotreitol (DTT) and 0.5% sodium dodecyl sulfate (SDS) to then be analysed with chip electrophoresis in a Caliper HT Protein LabChip system.

E.coli Lysate

To foul the media E.coli homogenate was used. Frozen E.coli homogenate was thawed and clarified through a glass fiber filter, followed by a 0.45 μm membrane filter.

Plate Experiments

Empty filter plates were filled with 20 μl gel per well. The method described in Table was used during the plate experiments. One plate was run with every solution in triplicate. The incubation time for the CIP was 15 minutes.

TABLE 11

Method for plate experiments

| Step | Volume (μl) | Buffer | Execution |
|---|---|---|---|
| Equilibration | 3x200 | PBS | Quick shake + vacuum |
| Fouling | 300 | E. coli | 30 min shake + vacuum |
| Wash | 3x200 | PBS | Quick shake + vacuum |
| CIP | 300 | See Appendix 1 | 15 min shake + vacuum |
| Wash | 3x200 | PBS | Quick shake + vacuum |
| Centrifugation | — | — | 5 min - 972xg, to remove all liquid |

After the end centrifugation of the beads the media plugs were transferred to a collection plate by connecting the collection plate on top of the filter plate and securing them together with rubber bands. The tower of plates was turned to have the filter plate on top and centrifuged for 5 min (972xg). 200 μl Caliper sample buffer was then added to all wells in the collection plate. The wells were covered with micro foil seal and put on a microplate shaker for 2 minutes. The plate was put in a heat chamber (104° C.) for 5 minutes. After heating the samples were additionally shaken for 2 minutes and centrifuged for 2 minutes (500×g) to sediment the gel particles. 40 µl of the supernatant was carefully transferred to a PCR plate (conical bottom). The order of samples were reversed during the transfer of gel plugs from the filter plate to the collection plate, here it was changed back by pipetting the samples in row H to row A and so on.

The PCR plate was centrifuged for 1 minute (500×g) to spin down gel particles that might have been transferred. The plate was then ready to be put in the Caliper chip electrophoresis equipment (Caliper Life Sciences Inc., USA)

Caliper LabChip Electrophoresis

The chip, buffer strip and the molecular weight ladder was prepared according to the HT Protein LabChip™ Kit user guide (Caliper Life Sciences Inc.,Nov. 2010). The HT Protein Express 200 High Sensitivity program was run.

Figure 4:
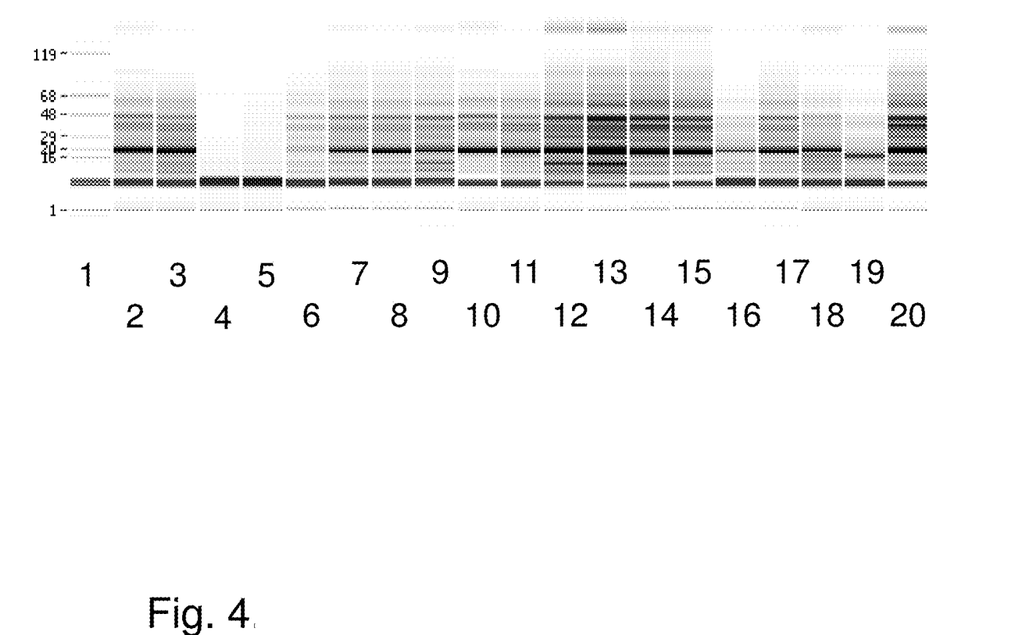
Figure 5:
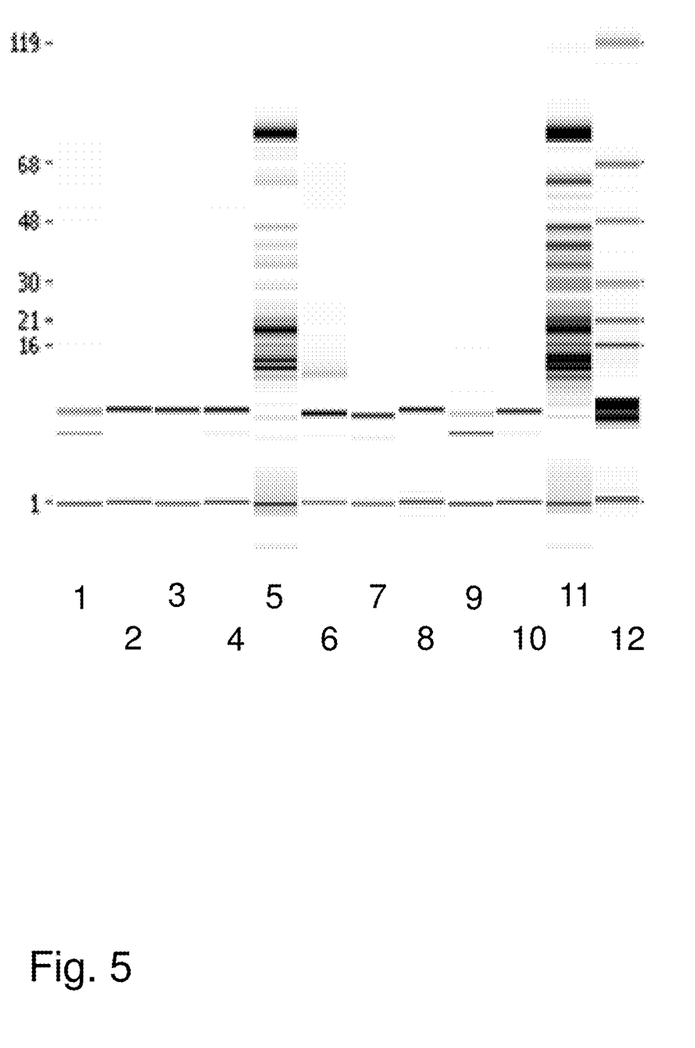
FIG. 5 shows chip electrophoresis data for extracts of *E Coli*-fouled polyallylamine prototype after regeneration with different regeneration solutions. Lanes: 1—1 M NaOH; 2—2 M NaOH; 3—1 M NaOH+30% 2-propanol; 4—1 M NaOH+20% 1-propanol; 5—8 M urea; 6—8 M urea+0.1 M citric acid; 7—6 M guanidinium hydrochloride; 8—0.5 M NaOH+1M NaCl; 9—1M NaOH/10 mM HCl/0.5M NaOH; 10—1M urea/1M NaOH; 11-No regeneration; 12-Mw markers.
Figure 6:
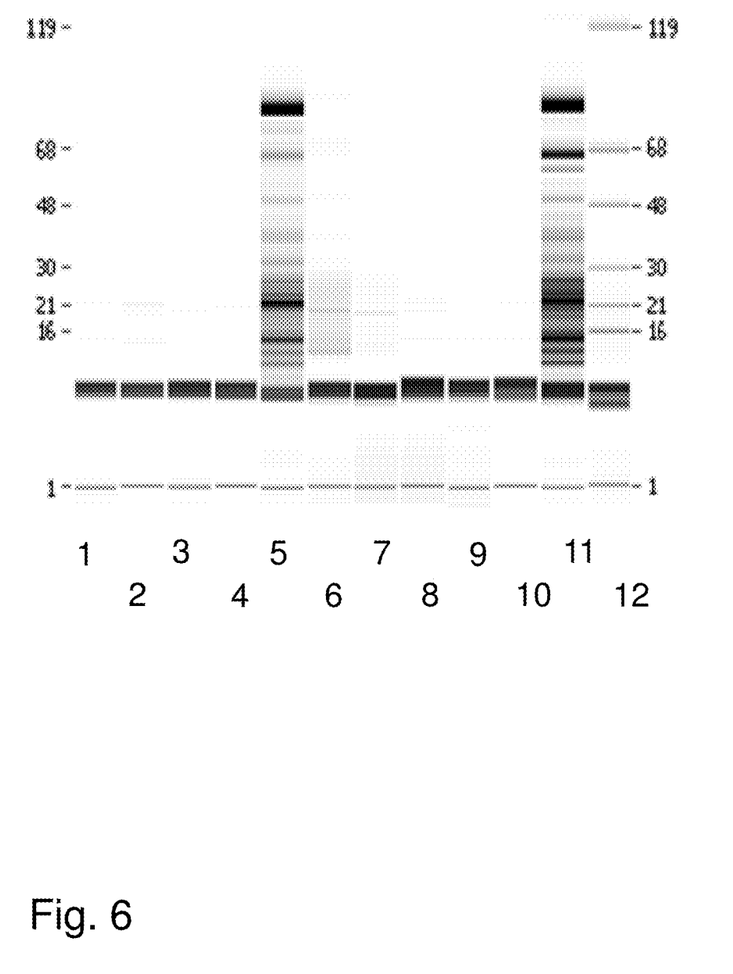
FIG. 6 shows chip electrophoresis data for extracts of *E Coli*-fouled tris(2-aminoethyl)amine prototype after regeneration with different regeneration solutions. Lanes: 1—1 M NaOH; 2—2 M NaOH; 3—1 M NaOH+30% 2-propanol; 4—1 M NaOH+20% 1-propanol; 5—8 M urea; 6—8 M urea+0.1 M citric acid; 7—6 M guanidinium hydrochloride; 8—0.5 M NaOH+1M NaCl; 9—1M NaOH/10 mM HCl/ 0.5M NaOH; 10—1M urea/1M NaOH; 11-No regeneration; 12-Mw markers

The results are shown in FIGS. 4-6. On Capto Core 700, only the solutions containing isopropanol were really effective in removing all the contaminants In contrast, on the polyallylamine prototype all the solutions with the exception of 8 M urea showed an efficient impurity removal. Also the diaminopropanol and trisaminoethylamine prototypes could be efficiently cleaned with all solutions except 8M urea and 8M urea+ citric acid.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A separation matrix for purification of biological particles, comprising a plurality of particles having covalently attached ligands displaying at least two primary amines per ligand, the particle having a shell and an inner radial portion, surrounded by the shell, wherein the combined content of nitrogen and oxygen atoms in said ligands is at least 20 wt % and wherein;
   a) the inner radial portion of the particle comprises substantially evenly distributed at least 50 micromole/ml primary amines from the covalently attached ligands and
   b) the shell of the particle having an average thickness of 0.5 to 6% of the volume-weighted average diameter or the sphere-equivalent diameter of the plurality of particles, comprises substantially evenly distributed less than 20 micromole/ml primary amines from the covalently attached ligands,
   wherein the shell is formed by;
   contacting allyl modified polysaccharide particles with an amount of halogen for a period of up to 30 minutes, wherein the amount of halogen is equivalent to the amount of allyls in a shell of the particles, to form polysaccharide particles with a halogenated shell;
   washing the polysaccharide particles with a halogenated shell with water; and
   adding an aqueous alkaline solution to the washed polysaccharide particles with a halogenated shell to at least partially inactivate the halogenated shell to form intermediate polysaccharide particles comprising remaining allyl groups, wherein the thickness of the shell is also controlled by the reaction time with the halogen.

2. The separation matrix of claim 1, wherein said ligands are attached to the particle via secondary or tertiary amine links.

3. The separation matrix of claim 1, wherein the content of primary amine nitrogen in said ligands is at least 18 wt %.

4. The separation matrix of claim 1, wherein the ratio of displayed primary amines to the total amount of nitrogen atoms in said ligands is at least 0.5.

5. The separation matrix of claim 1, wherein said ligands are selected from the group consisting of tris(2-aminoethyl) amine and polyallylamine, attached via an amine.

6. The separation matrix of claim 1, wherein said ligands comprise polyallylamine of molecular weight at least 1 kDa.

7. The separation matrix of claim 6, wherein the polyallylamine is non-crosslinked.

8. The separation matrix of claim 1, wherein said particles are substantially spherical.

9. The separation matrix of claim 1, wherein the shell of the particle has a molecular weight cutoff for globular proteins of 60 to 1000 kDa.

10. The separation matrix of claim 1, wherein the shell of the particle has a molecular weight cutoff for globular proteins of 400-800 kDa.

11. The separation matrix of claim 1, wherein the halogen is bromine.

* * * * *